US008382728B1

(12) United States Patent
Gibson

(10) Patent No.: US 8,382,728 B1
(45) Date of Patent: Feb. 26, 2013

(54) EMERGENCY MEDICAL DISPENSER

(76) Inventor: Sam Gibson, Sharpsville, PA (US)

( * ) Notice: Subject to any disclaimer, the term of this patent is extended or adjusted under 35 U.S.C. 154(b) by 100 days.

(21) Appl. No.: 13/068,631

(22) Filed: May 16, 2011

Related U.S. Application Data

(63) Continuation-in-part of application No. 12/313,284, filed on Nov. 19, 2008, now abandoned.

(51) Int. Cl.

| | |
|---|---|
| ***A61F 13/00*** | (2006.01) |
| ***A61J 7/00*** | (2006.01) |
| ***A61M 35/00*** | (2006.01) |
| ***B65D 83/00*** | (2006.01) |

(52) U.S. Cl. ..................... 604/304; 206/524.7; 206/530; 206/532; 206/534.1; 206/540; 206/562; 206/803; 206/820; 206/828; 222/187; 222/403; 222/540; 222/630; 604/77; 604/310

(58) Field of Classification Search ........................ None
See application file for complete search history.

(56) References Cited

U.S. PATENT DOCUMENTS

| | | | | |
|---|---|---|---|---|
| 4,889,236 | A | 12/1989 | Bartell et al. | |
| 6,808,514 | B2 | 10/2004 | Schneider et al. | |
| 2002/0066690 | A1 | 6/2002 | Mattis et al. | |
| 2004/0159571 | A1 * | 8/2004 | Fagen et al. | 206/461 |
| 2007/0235350 | A1 | 10/2007 | Warlick | |

* cited by examiner

*Primary Examiner* — Jackie Ho
*Assistant Examiner* — Joshua Lee
(74) *Attorney, Agent, or Firm* — Harpman & Harpman

(57) ABSTRACT

An emergency medication storage and integrated single use device for providing oral dissolving medications strips in a convenient transparent transfer environment. A thin card size dispenser holds a single medicated strip in user access orientation positioned for direct card insertion to the user's mouth assuring proper dispensing of the medication in an emergency situation.

5 Claims, 3 Drawing Sheets

EMERGENCY MEDICAL DISPENSER

This is a continuation in part application of Ser. No. 12/313,284, filed Nov. 19, 2008 now abandoned.

BACKGROUND OF THE INVENTION

1. Technical Field

This device relates to medical dispensing devices that are carried to provide a single dose of medication in an oral form.

2. Description of Prior Art

Prior art devices of this type have been directed to a variety of medication transportation cases and dispensing modalities.

Such devices can be seen in U.S. Pat. Nos. 4,889,236, 6,808,514 and U.S. Patent Publications 2002/0066690 and 2007/0235350.

In U.S. Pat. No. 4,889,236 a card style medication package can be seen having a plurality of medication dosage on a blister pack configuration with date indicia associated with prescribed administration instructions.

U.S. Pat. No. 6,808,514 is directed to an emergency medical dispensing card having a housing with a removable dispensing carriage for injection or alternately oral dispensing of desired medication.

U.S. Patent Publication 2002/0066690 shows a flat pill case having a hinged lid covering a core with multiple number of pill pads each holding an individual pill for ease of extraction and use.

Publication 2007/0235350 discloses a wallet size medicament dispenser in which a carrying case the size of a credit card is disclosed having medications positioned between oppositely disposed two panel configuration forming the case for removal and use.

SUMMARY OF THE INVENTION

A self-contained emergency medical single dose dispensing device that provides for an on demand medication dispensing of orally applied medication in emergency situations. An easily transportable and accessible medication card having a strip of medicated water soluble dissolvable film suspended thereon by for maximum patient contact in oral applications by insertion of the card into the mouth of the user.

DETAILED DESCRIPTION OF THE INVENTION

Figure 1:
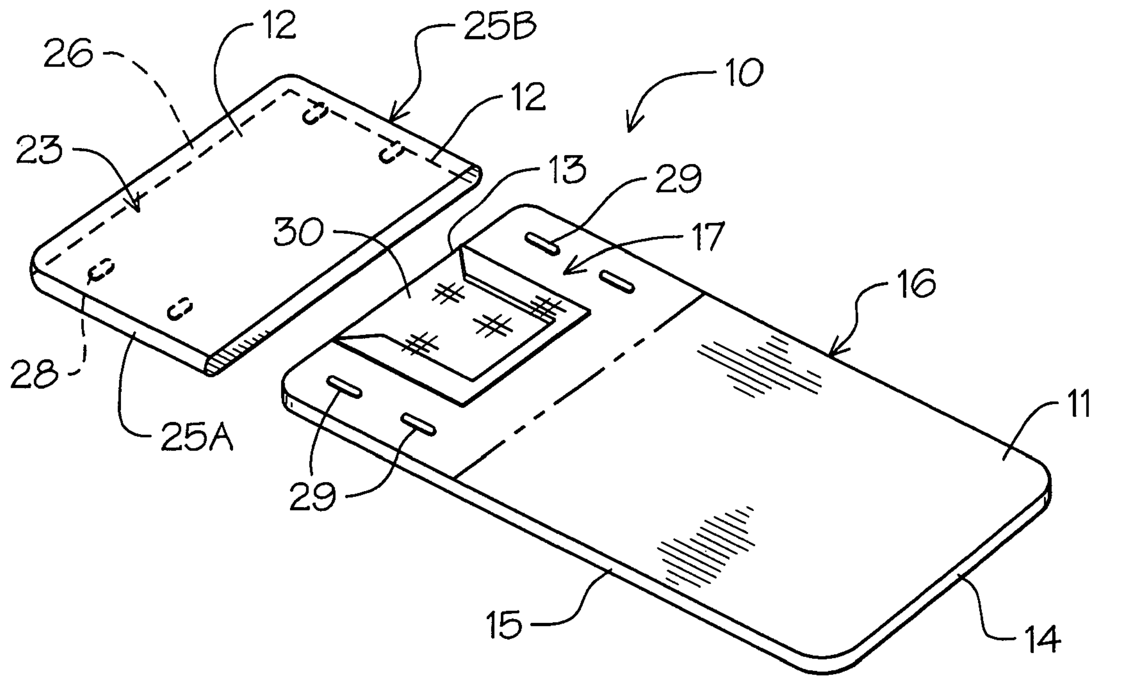
FIG. 1 is an exploded perspective view of the medication dispensing device of the invention.
Figure 2:
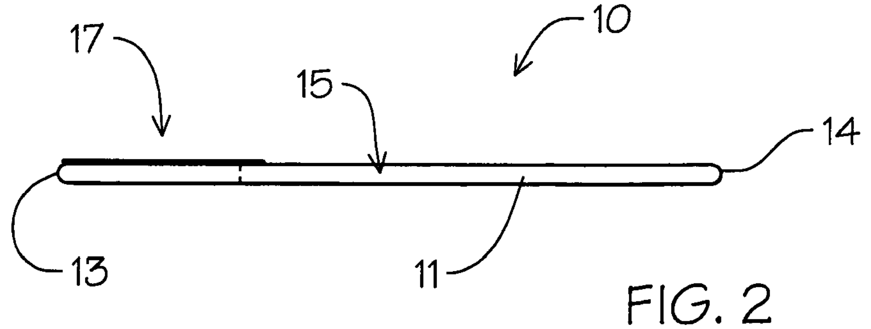
FIG. 2 is a front elevational view of a medical dispensing device.

Referring to FIG. 1 of the drawings, a medical dispensing device 10 of the invention can be seen having a main body portion 11 and a removable closure cap portion 12. The main body portion 11 is of an overall flat generally rectangular shape having parallel side end edges 13 and 14 in parallel spaced top and bottom edges 15 and 16. As noted, it is of a flat configuration emulating a classic credit card in general dimensions is well known within the art.

A medication dispensing area 17 is defined on the main body portion 11 inwardly of the end edge 13 by a pair of parallel spaced tab elements 18 and 19 each with effacing tapered surfaces 18A and 19A transitioning to corresponding opposing edge surfaces 20 and 21 forming a user engageable access depression depending notch at 22 therebetween within the main body member portion 11.

Closure end cap portion 12 is defined as having parallel spaced upper and lower surfaces 23 and 24 with interconnecting spaced parallel walls 25A and 25B and interconnecting end wall 26 with an access opening defined thereby.

Figure 3:
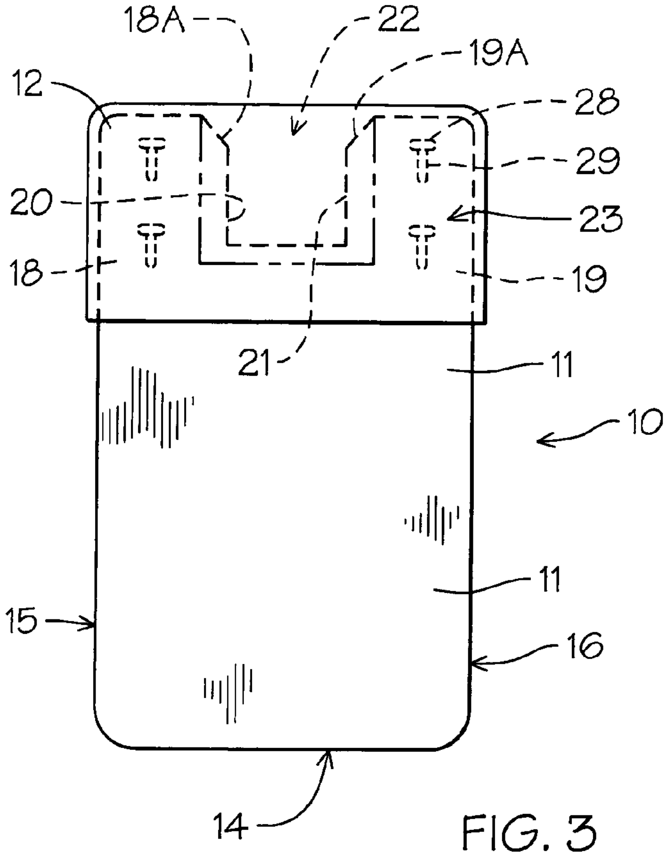
FIG. 3 is a top plan view thereof.
Figure 4:
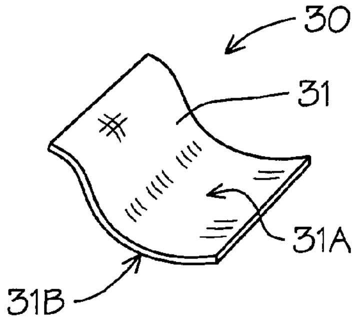
FIG. 4 is a perspective view of a dissolvable medication film strip of the medical dispensing device.
Figure 5:
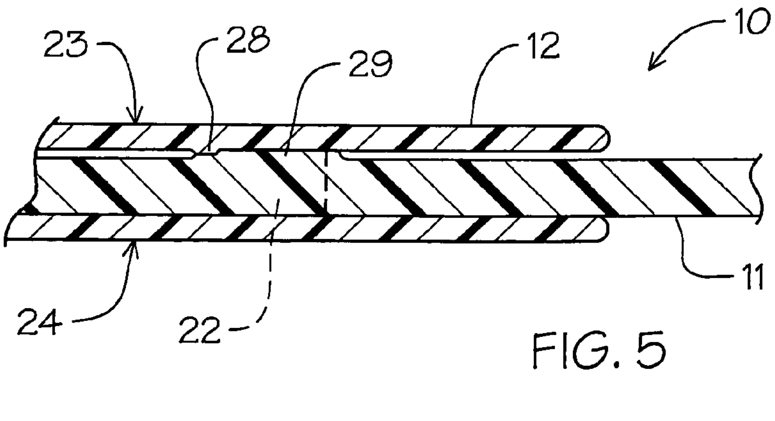
FIG. 5 is an enlarged partial cross-sectional view on lines 5-5 of FIG. 3.

The access opening is of an interior dimension greater than that of the corresponding transverse dimension of the main body portion 11 so as to be registerable thereover as illustrated in FIG. 3 of the drawings.

Registration retainment elements 28 may be provided on the interior surface of the end closure cap 12 that impart a frictional engagement with corresponding engagement elements 29 on the tab elements 19 and 20 retaining the end cap 12 in place thereover for storage, storage and transportation prior to emergency use. The corresponding engagement elements 28 and 29 also act as spacers for the cap 12 over the dispensing opening 22 as will be described in greater detail hereinafter.

A medication dispensing medium 30 for the dispensing device 10 is of a dissolvable thin flexible sheet medication absorbable transfer thermoplastic film strip 31 which is commonly used for a variety of over the counter oral aids such as breath fresheners and the like as is well known within the art. Such films 31 typically to be placed under the tongue, not shown, so that it will dissolve in seconds releasing the entrained medication such as aspirin for a quick assimilation into the patient's bloodstream. Such fast acting properties are well suited for medications needed in life threatening situations such as in heart attacks with aspirin or nitroglycerin, for example.

The dissolvable medication film strip 31 is secured on the upper surface of the main body portion 11 overlying the hereinbefore described dispensing opening 22 therein. This placement allows for maximum upper and lower surface areas 31A and 31B of the strip 31 to be exposed simultaneously to the moisture in a user's mouth (not shown) upon placement of the medical dispensing device 10 therein during emergency use.

In user venue, the medical dispensing device 10 has the closure cap 12 positioned in place over the dispensing opening 22 and suspended film strip 31 securing and protecting the aforedescribed film strip prior to required use.

In an emergency the user (not shown) retrieves the medical dispensing device 10, pulls the cap 12 off and inserts the device opening end first under their tongue. As noted, this placement fully exposes the suspended medicated film strip 31 for rapid almost simultaneous dissolving releasing the medication directly for rapid absorption into the patient's bloodstream.

Figure 6:
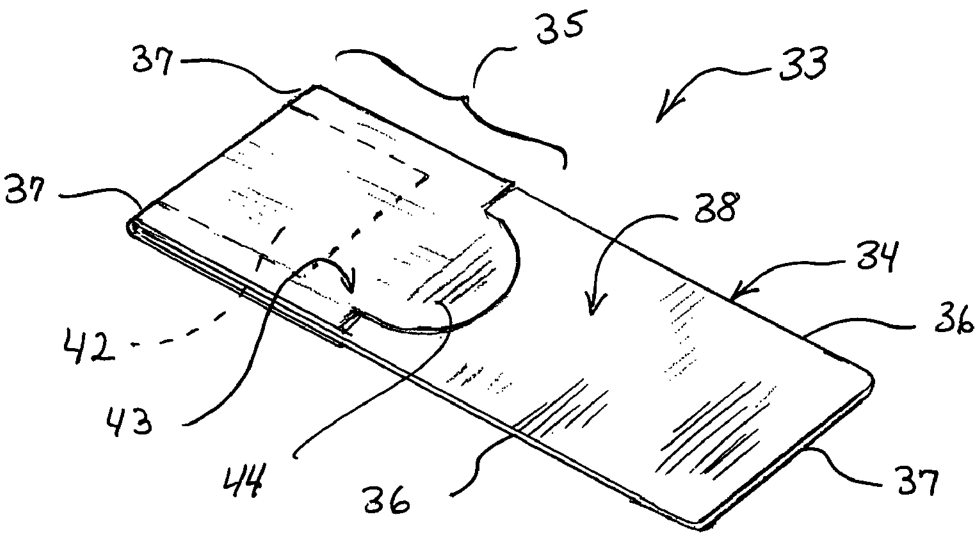
FIG. 6 is a perspective view of an alternate form of the invention.
Figure 7:
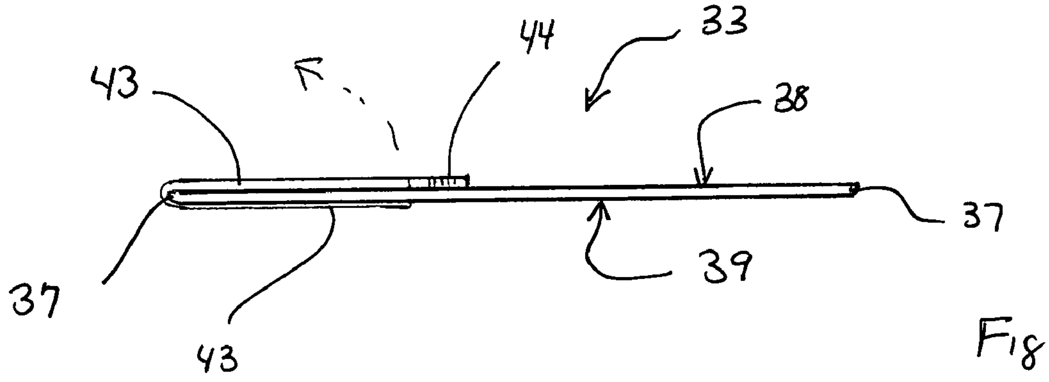
FIG. 7 is a side elevational view thereof.
Figure 8:
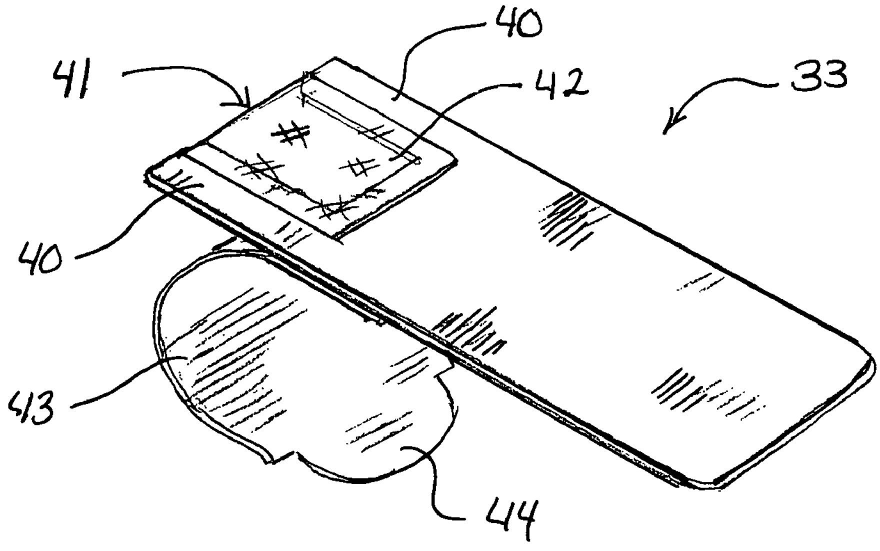
FIG. 8 is a perspective view thereof showing partial removal of safety wrap cover for use.

Referring now to FIGS. 6-8 of the drawings, an alternate form of the invention can be seen wherein a medical dispensing device 33 has a primary base member 34 with a medication support and dispensing portion 35. The base member 34 is of an overall flat generally rectangular shape having parallel sides 36 and oppositely disposed end edges 37 with flat top and bottom surfaces 38 and 39 respectively thereon.

The medical dispensing portion 35 has parallel spaced longitudinally extending medication support arms 40 defining a medication support opening at 41 therebetween. A medication dispensing medium 30' of the dispensing device 34 is of a dissolvable thin flexible sheet of medication absorbable transfer thermoplastic film strip 42 that dissolves upon contact with moisture releasing the medication entrained therein as is well known and understood within the art.

The film strip 42 is secured to respective portions of said arms 40 so as to overlie the opening 41 suspended between the arms 40. Once inserted into the mouth of the user (not shown) the film strip 42 will fully dissolve thereby dispensing the complete medication dose into the mouth of the user. After use, the device 33 is removed and discarded.

A thin flexible moisture resistant wrap 43 is removably attached overlying the dispensing portion 35 as best seen in FIGS. 6 and 7 of the drawings, wrapping around the ends 36 of the arms 40 completely sealing over the dispensing portion 35, opening 41 and the suspended medication dispensing medium 30' as hereinbefore described.

The wrap 43 has an engagement tab 44 extending from one end thereof to allow ease of user engagement and removal as illustrated in progress in FIG. 7 of the drawings for emergency use.

It will be evident from the above description that the one time emergency use medical dispensing devices 10 and 33 will provide for a safe, simple and rapid means of dispensing a single dose of potentially life saving medication for a patient which can be quickly and easily accessed and self-administered for rapid dispersion into the patient's bloodstream and the therapeutic effect of the medication can be achieved.

It will thus be seen that a new and useful emergency single dose medication dispensing device has been illustrated and described and it will be apparent to those skilled in the art that various changes and modifications may be made thereto without departing from the spirit of the invention.

Therefore I claim:

1. An emergency medical medication dispensing device for oral use comprising, a main flat body member, oppositely disposed spaced parallel arm elements extending from said main body member, an application dispensing opening between said arm elements, a soluble medication transfer strip secured to said arms and suspended over said opening, said medication transfer strip dissolvable while mounted on said arm elements when in direct contact with moisture, a thin flexible moisture resistant wrap removably covering said arm elements and said medication transfer strip suspended thereby.

2. The emergency medical medication dispensing device of claim 1 wherein said main flat body member is of a rectangular dimension.

3. The emergency medical medication dispensing device set forth in claim 1 wherein said medication transfer strip is of a film configuration and of an overall dimension greater than that of said dispensing opening.

4. The emergency medical medication dispensing device of claim 1 wherein said wrap extends over a portion of said main body member beyond said application dispensing opening having a user engagement tab extending therefrom.

5. The emergency medical medication dispensing device of claim 1 wherein said wrap is selectively retained on said body member and arm elements by a pressure release adhesive.

* * * * *